United States Patent [19]
Caselli

[11] Patent Number: 5,201,710
[45] Date of Patent: Apr. 13, 1993

[54] SYRINGE FITTED WITH A CLAMPING DEVICE FOR THE NEEDLE AND WITH MEANS TO ENABLE THE NEEDLE TO BE AUTOMATICALLY RETRACTABLE INTO THE SYRINGE BODY AT THE END OF AN INJECTION

[76] Inventor: Paolo Caselli, Via Fiesole, 42, 47023 Cesena (Forli), Italy

[21] Appl. No.: 845,965

[22] Filed: Mar. 4, 1992

[30] Foreign Application Priority Data

May 29, 1991 [EP] European Pat. Off. ........ 91830226.6

[51] Int. Cl.⁵ .............................................. A61M 5/00
[52] U.S. Cl. ..................................... 604/110; 604/195
[58] Field of Search ............... 604/110, 187, 195, 198, 604/263

[56] References Cited

U.S. PATENT DOCUMENTS

| | | |
|---|---|---|
| 4,687,467 | 8/1987 | Cygielski . |
| 4,826,491 | 5/1989 | Schramm ...................... 604/263 X |
| 4,994,034 | 2/1991 | Botich . |
| 5,000,736 | 3/1991 | Kaufhold et al. . |
| 5,049,133 | 9/1991 | Villen Pascual ................ 604/110 |
| 5,053,010 | 10/1991 | McGary et al. ................ 604/110 |
| 5,084,018 | 1/1992 | Taso ................................ 604/195 X |

FOREIGN PATENT DOCUMENTS

| | | |
|---|---|---|
| 0413414 | 2/1991 | European Pat. Off. . |
| 9104066 | 4/1991 | World Int. Prop. O. . |
| 9105578 | 5/1991 | World Int. Prop. O. . |

*Primary Examiner*—John D. Yasko
*Attorney, Agent, or Firm*—Stevens, Davis, Miller & Mosher

[57] ABSTRACT

A syringe fitted with a clamping device for the needle and with means to enable the needle to be automatically retractable into the syringe body at the end of an injection comprises: outer and inner cylinders; openings at the ends of the outer cylinder; a third opening at an end of said inner cylinder; closing means for said third opening; a needle with a head; sealing means in said closing means; a first spring to push said needle against said closing means; a clamping device loaded by a second spring to maintain outward said syringe and to release said needle; a diaphragm in said closing means which bends before its breaking; a sharp element to break said diaphragm; closing means to prevent said needle from being reached and stopping means to prevent said second cylinder from being moved outward said syringe after its use.

10 Claims, 10 Drawing Sheets

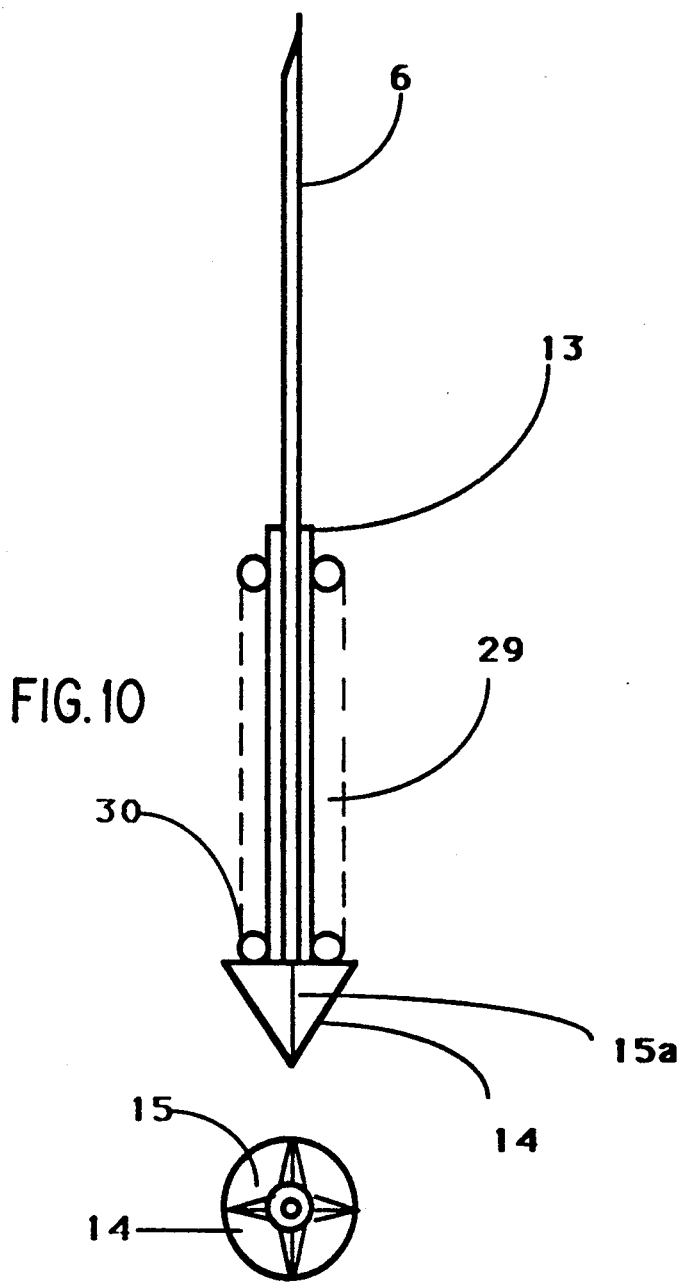

SYRINGE FITTED WITH A CLAMPING DEVICE FOR THE NEEDLE AND WITH MEANS TO ENABLE THE NEEDLE TO BE AUTOMATICALLY RETRACTABLE INTO THE SYRINGE BODY AT THE END OF AN INJECTION

The present invention relates to a syringe fitted with a clamping device to clamp the needle at a position of injection and with means which enable the needle to be retractable into the body of the syringe at the end of the injection.

BACKGROUND OF THE INVENTION

Syringes fitted with means to retract automatically the needle at the end of the injection are known.

One of these syringes is shown in Edward F. Allard, U.S. Pat. No. 4,838,869, which is related to a hypodermic needle which retracts into the body of the syringe after use, thereby preventing the reuse and the spread of diseases normally associated therewith. This syringe comprises outer and inner cylinders wherein the outer cylinder has a first end with a first opening for effecting the protusion of said needle and a second end with a second opening allowing for the moving of the inner cylinder through the outer cylinder. The inner cylinder is located within the confines of the outer cylinder for receiving and storing the needle when retracted.

Plunger means are in slidable contact with the inner wall of the outer cylinder for effecting a vacuum inside the syringe upon actuating the plunger in an outward direction, whereby a fluid may be drawn into the outer cylinder and expelled upon actuating the plunger inwardly.

The needle which extends through the second opening of the outer cylinder has a head somewhat larger than the diameter of the needle to establish a rim that can be used to firmly hold the needle in place during use by holding tabs within the first end of the outer cylinder; the needle is spring loaded, whereby upon contacting the holding tabs with the end of the plunger the spring loaded needle is caused to be disengaged and retracted into the inner cylinder for storage.

The problems which the syringe device shown in U.S. Pat. No. 4,838,869 does not solve are the following:

1—To allow the syringe to be completely emptied out.

2—To shear the closing element placed in the opening of the second cylinder housed by the first cylinder.

3—To prevent the needle from being easy reached after use of the syringe.

4—To place sealing means at a suitable position in order to prevent the fluid to be injected from being transferred into a cavity which houses the head of the needle.

5—To properly dispose the needle with respect to the outer cylinder.

6—To allow the inner cylinder to be clamped by the outer cylinder in order to prevent the needle from being easy reached after use of the syringe.

AIM OF THE INVENTION

The present invention, as claimed, is intended to remedy these drawbacks. It solves the problem of creating a syringe fitted with a clamping device for the needle and with means to enable the needle to be automatically retractable into the syringe body at the end of an injection. By using a syringe according to the present invention the following results are achieved: the needle is maintained in a right position before the injection by pliers means which clamp automatically the same needle; said pliers means allowing the needle to be retracted into the body of the syringe and to close any entry of the syringe at the end of the injection.

Furthermore all the fluid is injected into the body of the patient and the entry of the needle into second cylinder of the syringe is made easy by a sharp element disposed at the basis of the head of the same needle.

The advantages offered by the invention are mainly that the inner cylinder is clamped by the outer cylinder at the end of the injection thus preventing the needle from being easily reached after use of the syringe.

BRIEF DESCRIPTION OF THE DRAWINGS

One way of carrying out the invention is described in detail below with reference to drawings which illustrate only one specific embodiment, in which:

FIG. 10 shows a needle fitted with a sharp part having four points.

FIG. 11 shows an end view of the needle as depicted in FIG. 10.

DESCRIPTION OF THE PREFERRED EMBODIMENT

Figure 1:
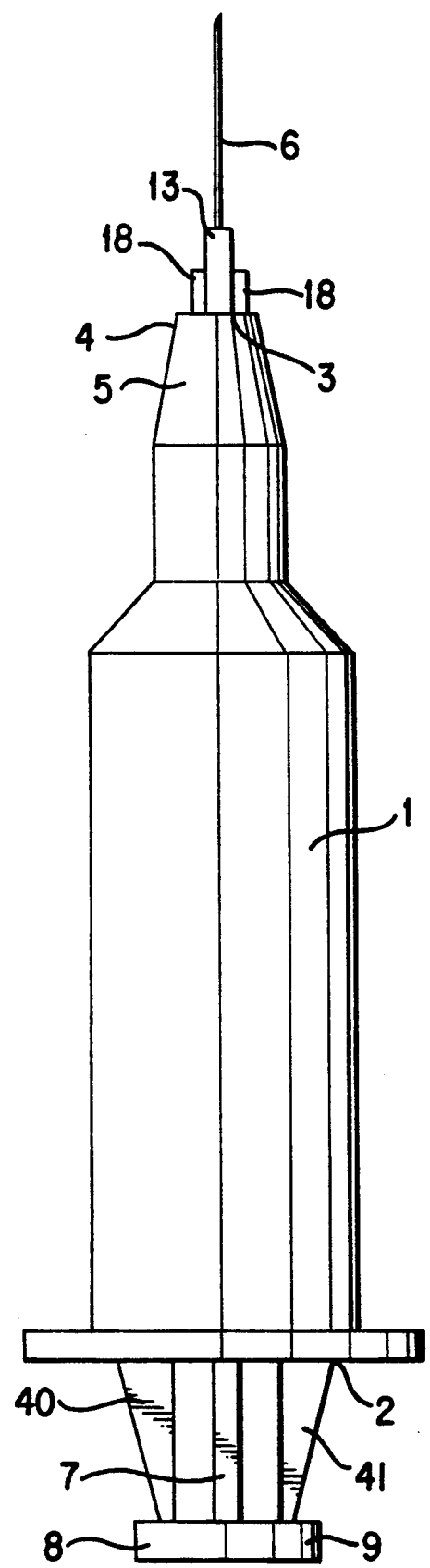
FIG. 1 is a vertical section view of a syringe according to the present invention.

The syringe shown in the FIGS. comprises a first outer hollow cylinder 1 having a longitudinal symmetry axis, a first opening 2 and a second opening 3; this latter is located at an end 4 of a cylindrical hollow piece 5 which extends on the outside of the cylinder 1; a needle 6 protrudes outward the syringe through the second opening 3.

A second hollow cylinder 7 is housed in the first cylinder 1 through the opening 2; the second cylinder 7 is coaxial with the first cylinder 1 and has an external end 8 made by a closing element 9, which enables to push the cylinder 7 in the direction of injection.

Figure 2:
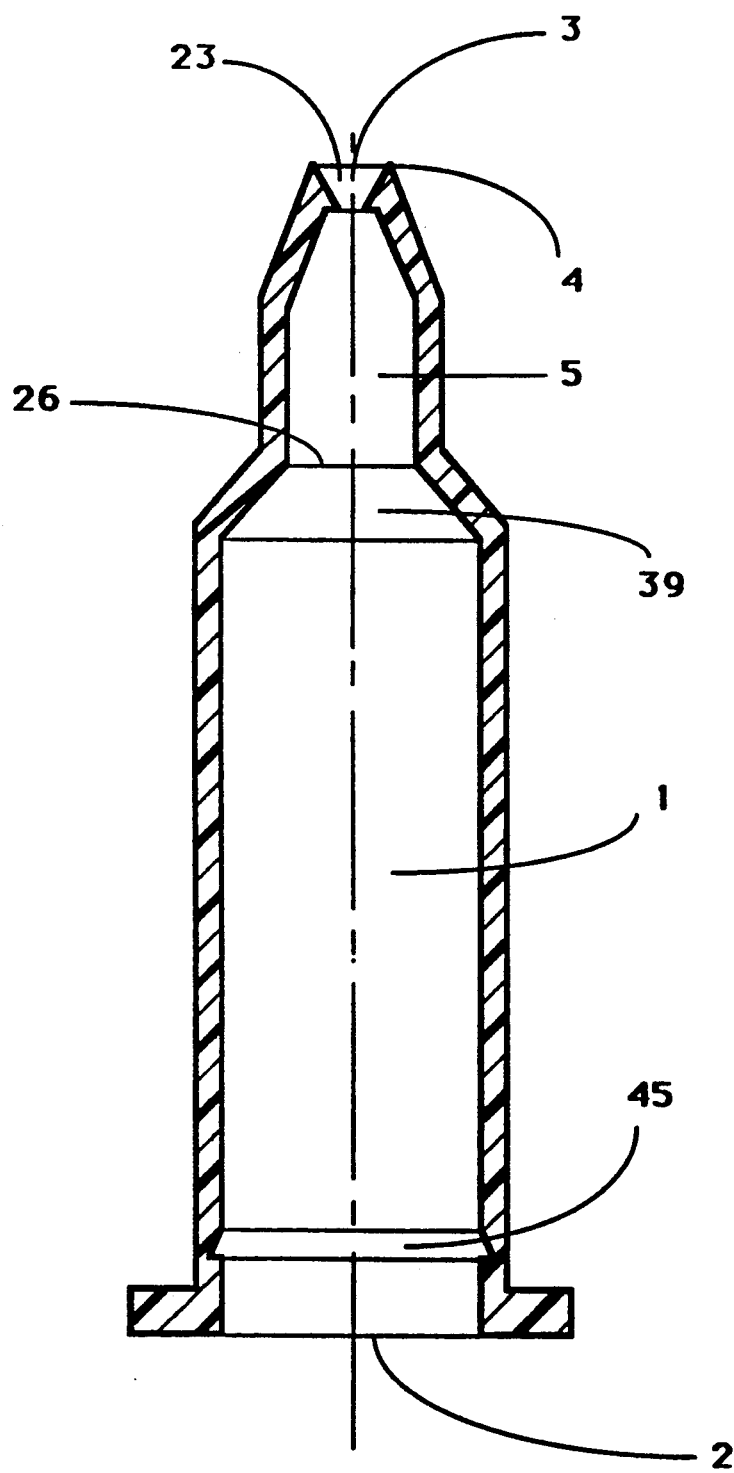
FIG. 2 is a vertical section view of an outer cylinder of the syringe.

A second end 10 of cylinder 7 shows an opening 11 facing inside first cylinder 1 and which may be closed by a sealing and closing element 12, better shown in FIG. 2.

The needle 6 is partially housed in a covering 13 shaped like a tube, which shows a head 14 inside the first cylinder 1, the head 14 being fitted with a sharp part 15 shaped like a crown with a sharp edge or with a push-rod with four sharp parts 15, whose dimensions depend on the dimensions of the syringe.

Preferably the covering 13 is an aluminum covering and presents a milled lateral surface 16 to increase the friction between two metal surfaces in contact. Furthermore the covering 13 houses a part of the needle 6 with precision.

In a not shown embodiment of the invention the covering 13 is a plastic covering or a synthetic resin covering, the friction coefficient of which is high.

Advantageously the opening 3 presents a seat 23 which widens from the inside to the outside of the syringe in order to cooperate with a spring 21 to clamp parts 18 of a pliers element 17 on the milled surface 16, the spring 21 being able to stress the pliers element 17 toward the inside of the syringe.

The pliers element 17 comprises three elastic parts 18; consequently it is able to clamp the covering 1 when the parts 18 adhere to the seat 23 and to release it when the parts 18 are moved away from the seat 23.

The pliers element 17 is made by a cylindrical body 19 substantially housed by the inside of the hollow piece 5; three parts 18 of the pliers element 17 are integral with the body 19.

The outside of the body 19 presents a circular crown 20 on which leans a first end of a spring 21, a second end of which leans on an annular surface 23 provided in the part of the hollow piece 5 near the opening 3. The shape of three parts 18 enables the true clamping of the covering 13 with respect to the symmetry axis of the cylinder 1.

A gasket 24 is located between the outer surface of the body 19 and the inner surface of the piece 5, said gasket being fitted with radial cuts for the passing of the fluid from the cylinder 1 through radial cuts provided in the head 14. More precisely the gasket 24 is located in an opening 26 between the cylinder 1 and the piece 5 to prevent the fluid from passing from the cylinder 1 into the hollow piece 5

Figure 3:
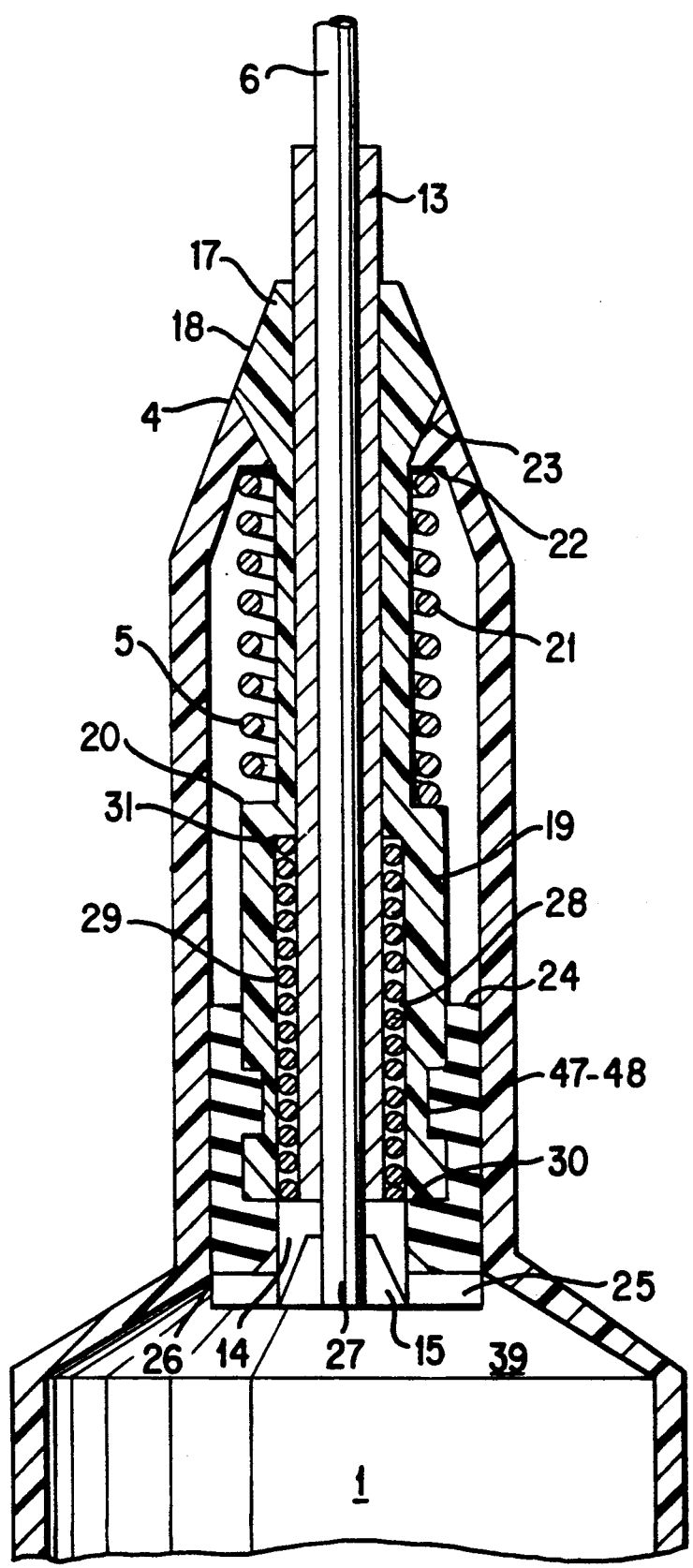
FIG. 3 is a partial section view of the syringe.
Figure 4:
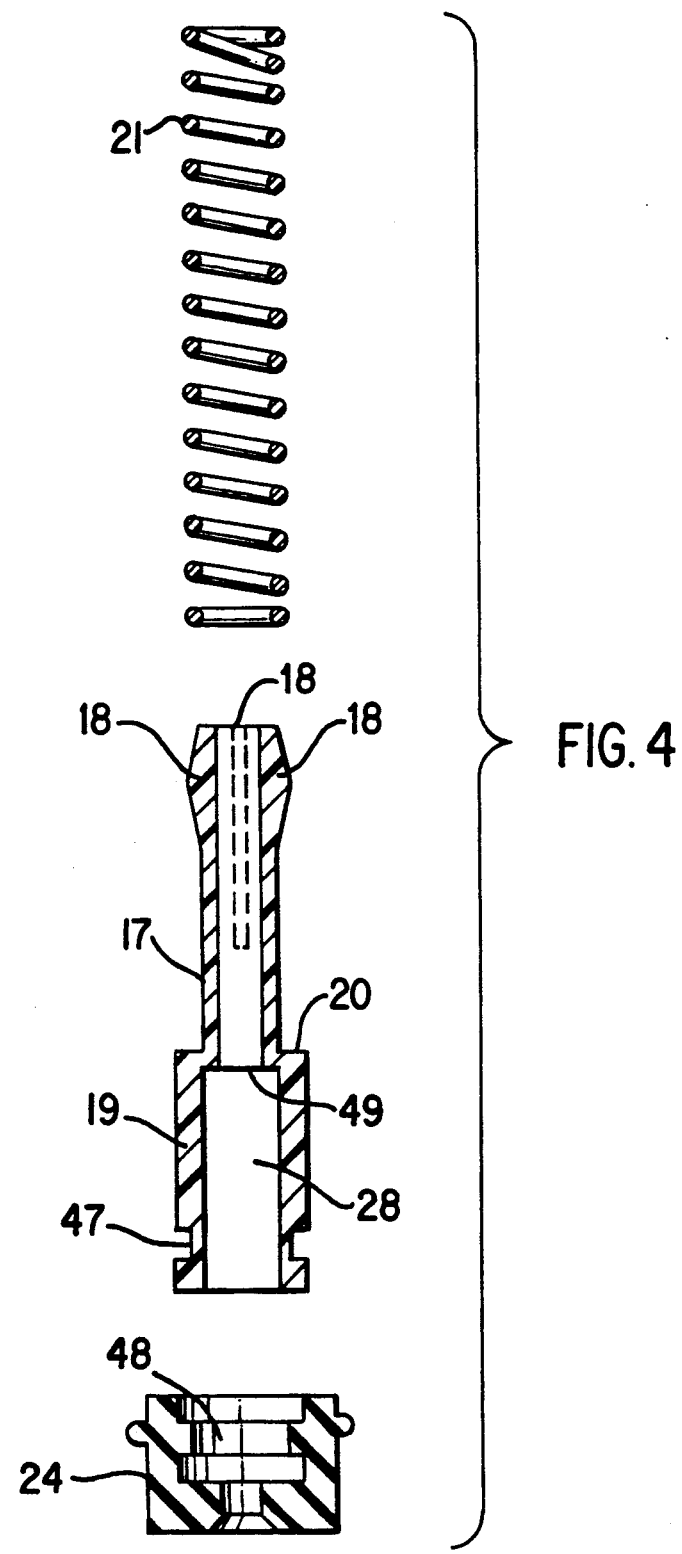
FIG. 4 is an exploded view of a constructive detail of the syringe.
Figure 5:
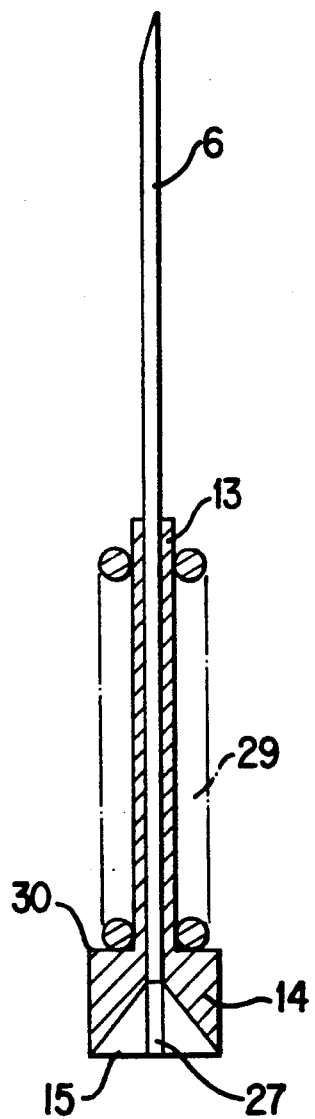
FIG. 5 is a cross-section view of the needle, of its head and of a covering comprising a sharp part.
Figure 6:
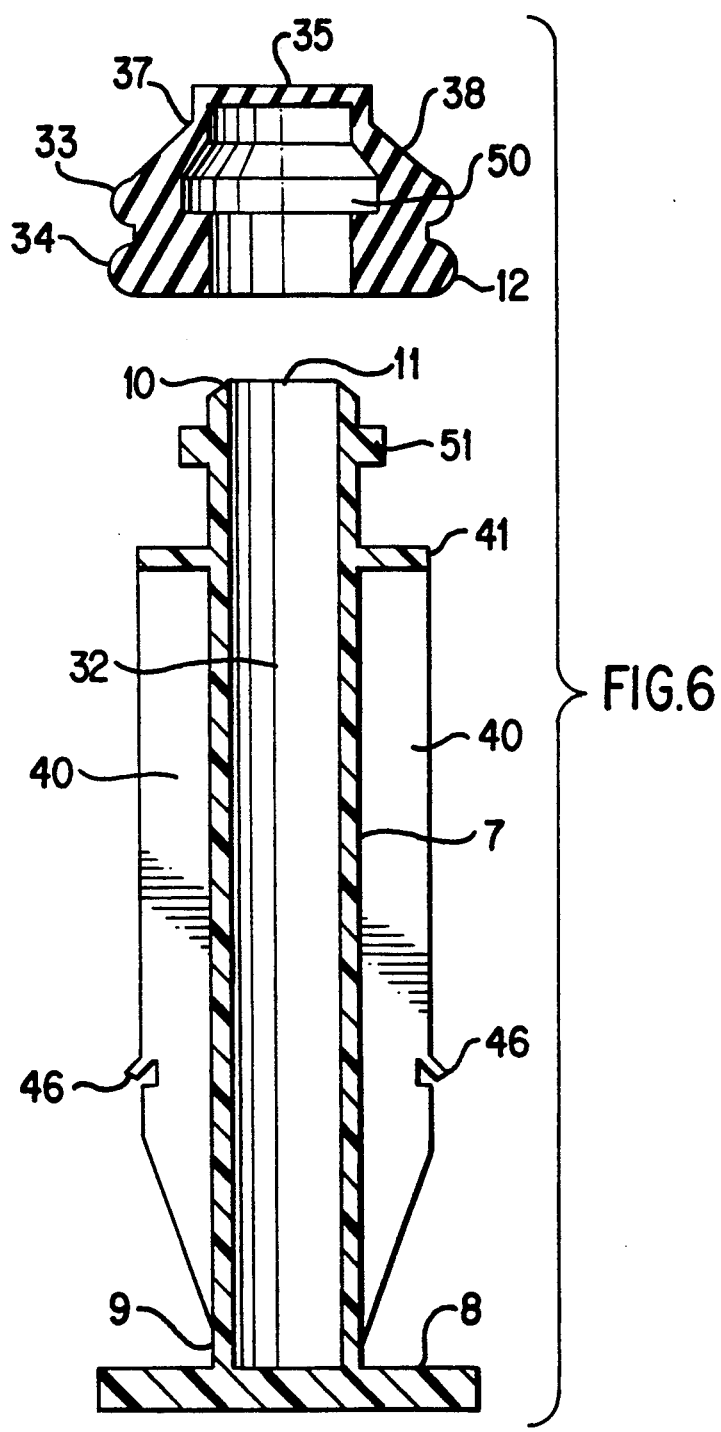
FIG. 6 is an exploded view of the inner cylinder and of the gasket which closes an opening of the same cylinder.
Figure 7:
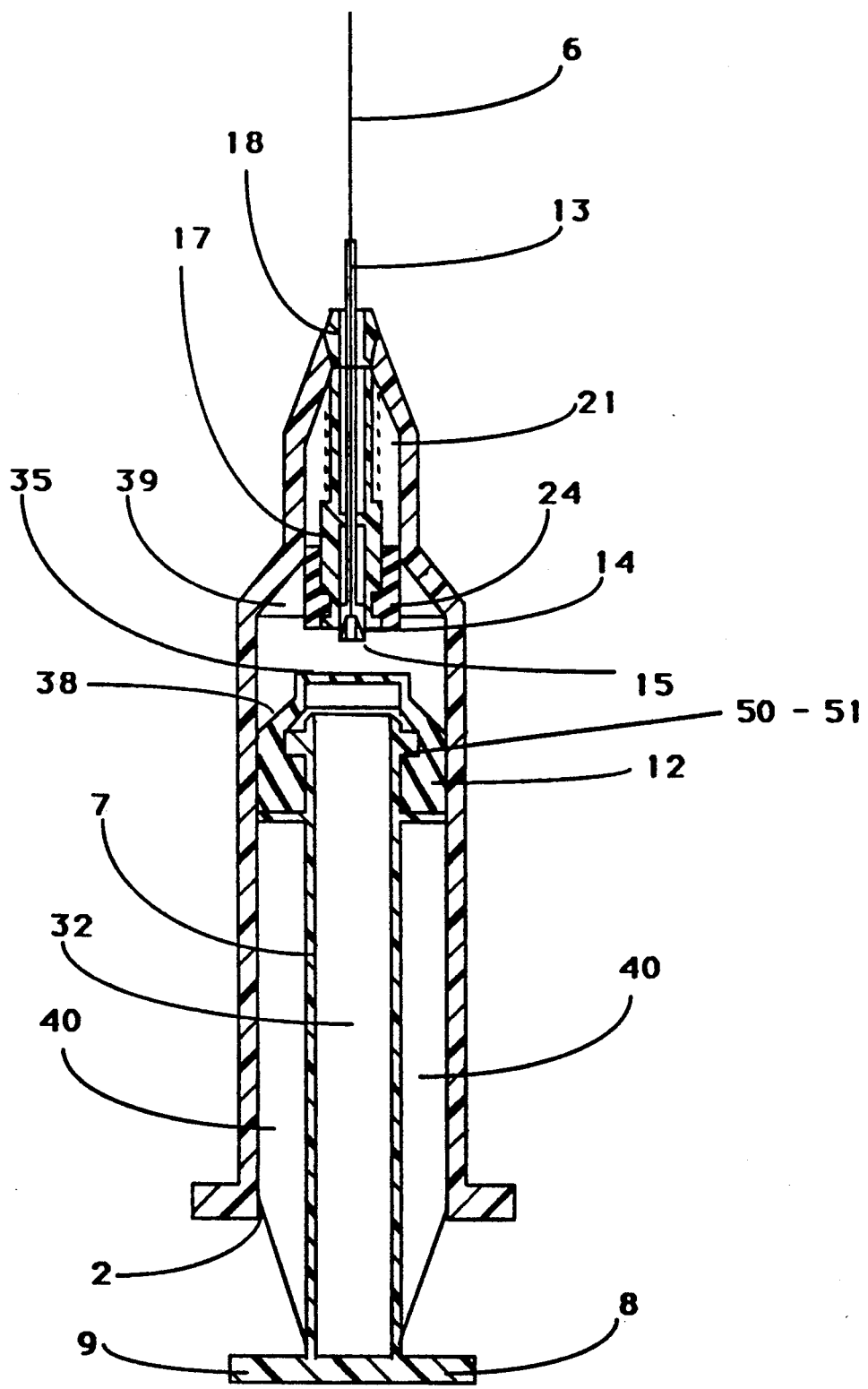
FIG. 7 is a front view of the syringe.
Figure 8:
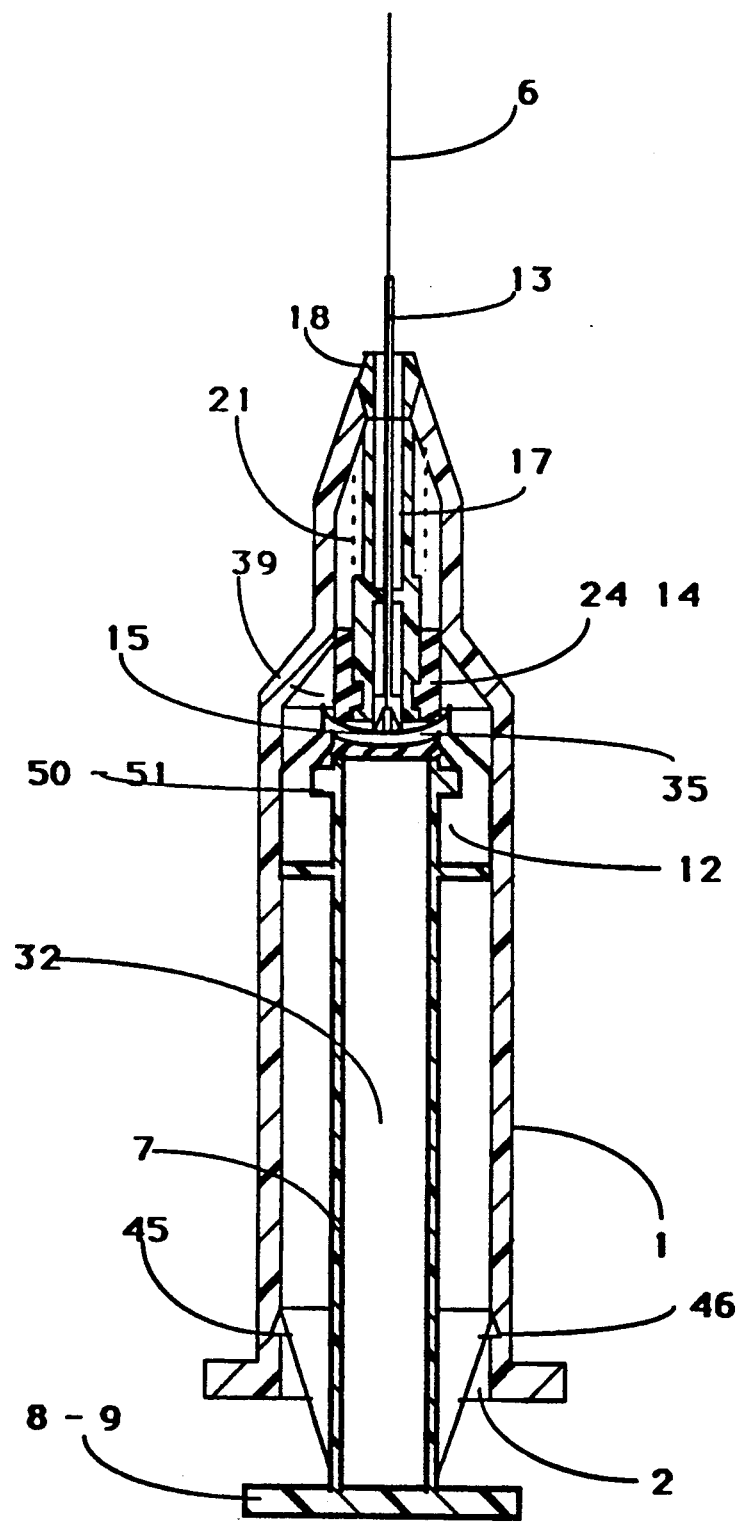
FIG. 8 shows the syringe before the end of the injection.
Figure 9:
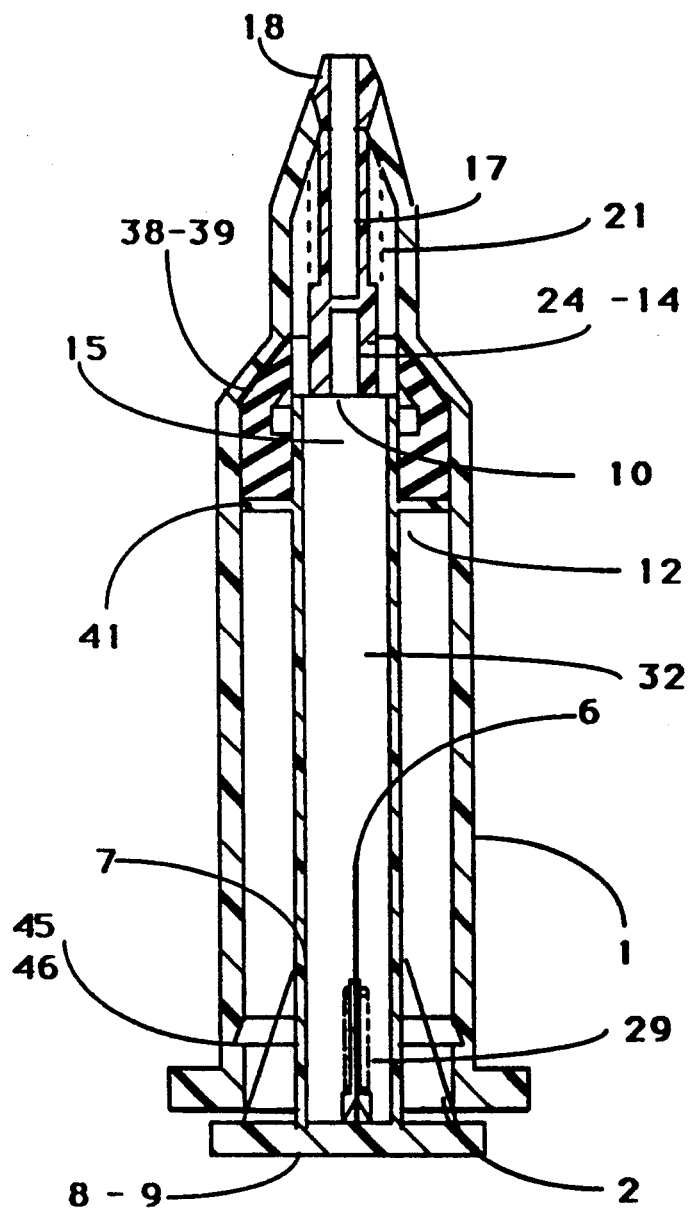
FIG. 9 is a partial view of the syringe after use.

The embodiment shown in FIG. 3 shows the sharp part 15 which protrudes easy into cylinder 1, the covering 13 which passes through a cavity 28 with which it is coaxial, said covering 13 protruding in the outside of the syringe by passing through the pliers element 17 which clamps it. Further a spring 29 is located between an annular surface 30 of the head 14 and an annular surface 31 of the cavity 28 near the opening 2, said spring 29 being able to push toward the inside of the cylinder 1 the covering 13 and the needle 6 housed in the same covering 13.

The second cylinder 7 shows a longitudinal cavity 32 able to house the needle 6; this cavity 32 is closed by the element 12 which is sliding inside the cylinder 1 to enable the motions of the cylinder 7 in the directions of suction and of injection of the fluid. For this reason the element 12 is fitted with two sealing rings 33 and 34 which prevent the fluid from passing into the part of the cylinder 1 between the element 12 and the opening 2.

The element 12 is fitted with a diaphragm 35 which closes the opening 11, the diaphragm 35 being able to bend when stressed by the sharp part 15 before its breaking by means of the same sharp part 15. In this way the syringe is completely emptied out.

For this reason the diaphragm 35 is disposed at the end of a cylindrical piece 36 which protrudes from the element 12 toward the opening 3. The basis of the piece 36 is connected with a surface 37 of the element 12 shaped like a truncated cone and having an inclination which is identical with the inclination of a bottom wall 39 of the outer cylinder 1 and which is the limit stop of the motion of the cylinder 7 in the direction of injection. These inclinations and the shape of the diaphragm 35 allow the syringe to be completely emptied out at the end of the stroke of the cylinder 7 in the direction of injection.

The second cylinder 7, the diameter of which is smaller than the diameter of the first cylinder 1, is integral with four ribs 40 which extend longitudinally in the direction of the symmetry axis of the cylinder 7 between a stopping cap 41 for the element 12 and the closing element 9 of the external end of the cylinder 7.

To maintain the element 12 in the position which enables the translation movements within the cylinder 1 and prevents the fluid from passing into the part of the cylinder 1 between the opening 2 and the element 12, a ring 42 is located between the cap 41 and the opening 11, the ring 42 being housed by an annular groove 43 made in the internal part of the element 12.

To stop the translation movements of the second cylinder 7 within the first cylinder 1 are provided stopping means 44 made by an annular groove 45 in the lateral inner wall of the first cylinder 1 and by teeth 46 made in the ribs 40.

The groove 45 is tapared in the direction which joins the opening 2 with the opening 3; in this way the teeth 46 enable the cylinder 7 to be translated toward the opening 3, by limiting the translation toward the opening 2 for the filling up of the syringe.

RUNNING OF THE INVENTION

The running of the syringe according to the present invention will be explained below.

Before the injection the syringe is in the position shown in FIG. 2; to enable the fluid to be sucked into the syringe the cylinder 7 is moved toward the head 14 of the needle 6 without any effort. The translation of the cylinder 7 toward the opening 2 allows the entry of the fluid into the part of the cylinder 1 between the gasket 24 and the element 12.

During the injection the cylinder 7 is moved toward the opening 3 to inject the fluid into a part of the body of the patient.

When the external surface of the diaphragm 35 touches the sharp part 15 the cylindrical piece 36 starts bending to allow the surface 37 to be brought into contact with the bottom wall 39 of the cylinder 7 in order to allow the syringe to be completely emptied out.

At the end of the translation of the cylinder 7 toward the opening 3 the element 12 moves the gasket 24 stressed by the spring 21 toward the opening 3, since the gasket is integral with the body of the pliers element 17, this latter moves outward the syringe and three parts 18 of the pliers element 17 move away from the seat 23 and open; in this way the covering 13 and the needle 6 are free. The spring 29 pushes the covering 13 and the needle 6 against the diaphragm 35; in that way the sharp element 15 may break the diaphragm 35 and open the opening 11.

At the end of this operation the needle 6 is inside the cylinder 7 and the parts 18 of the pliers 17, which are closed again under the action of the spring 21, prevent a hand from being inserted in the syringe through the opening 3.

The motions of the cylinder 7 toward the opening 2 are limited by the teeth 39 housed in the groove 38; thus the syringe may be not opened at the end of the injection.

I claim:

1. A syringe fitted with a clamping device for a needle and with means to enable said needle to be automatically retractable into the syringe body at the end of an injection comprising: a first outer cylinder and a second inner cylinder, said second cylinder having a cavity; a first and a second opening at the ends of said first cylinder, said second opening having a seat which widens from the inside to the outside of the syringe; a third opening at an end of said second cylinder, said third opening being for the entering into said cavity of said second cylinder; closing means for closing said third opening in order to enable said second cylinder to operate as a plunger, said closing means comprising diaphragm means; a needle extending outward a syringe and being able to be housed in said cavity of said second cylinder, said needle being provided with a head, and piercing means cooperating with said head to pierce said closing means; sealing means in said closing means to prevent a fluid from being transferred into a part of said first cylinder between said closing means and said first opening; a spring device able to push said needle against said closing means to pierce said closing means and to push said needle toward the cavity of said second cylinder; and a clamping device stressed by spring means;

wherein
said clamping device is able to move outward said syringe; said clamping device being fitted with elastic parts which cooperate with said seat to clamp said needle in order to maintain said needle outward said syringe when said spring means are compressed and to release said needle when said spring means are extended; at the end of the translation of said second cylinder toward said second opening of said first cylinder said second cylinder pushing said clamping device outward said syringe to move said elastic parts away from said seat in order to release said needle.

2. A syringe as claimed in claim 1, wherein said clamping device is a pliers device comprising three elastic parts able to clamp true said needle with respect to the symmetry axis of said syringe.

3. A syringe as claimed in claim 1, wherein said needle is partially housed in a covering shaped like a tube which shows a head inside said first cylinder; said covering housing a part of said needle with precision.

4. A syringe as claimed in claim 1, wherein said clamping device presents a hollow; a first part of said hollow facing the outside of said syringe being closed by said covering; a second part of said cavity facing the inside of said syringe being closed by said head; said hollow housing said spring device between an annular surface of said head and an annular surface made in a part of said hollow near said second opening.

5. A syringe as claimed in claim 1, wherein said diaphragm means are disposed at the end of a cylindrical piece which protrudes from said closing element toward said opening of said first cylinder.

6. A syringe as claimed in claim 5, wherein a surface shaped like a truncated cone is disposed in said closing element, said surface having an inclination which is identical with the inclination of a bottom wall of said first cylinder; said bottom wall being the limit stop of the motion of said second cylinder in the direction of injection; said inclinations and said shape of said closing element allowing the syringe to be completely emptied out at the end of the stroke of said second cylinder in the direction of injection.

7. The syringe of claim 1, wherein said stopping means are made by an annular groove in the lateral inner wall of said first cylinder and by teeth provided in ribs integral with said second cylinder; said annular groove being tapared in the direction which joins said first opening with said second opening in order to enable said teeth to make said cylinder translate toward said second opening, by limiting this translation toward said first opening for the filling up of the syringe.

8. A syringe as claimed in claim 3, wherein said covering has a milled lateral surface to increase the friction between said elastic parts in clamping position and said lateral surface.

9. A syringe as claimed in claim 3, wherein said pliers device presents a hollow, a first part of said hollow facing the outside of said syringe being closed by said covering, and a second part of said hollow facing the inside of said syringe being closed by said head; said hollow housing said spring device between an annular surface of said head and an annular surface made in a part of said hollow near said second opening.

10. A syringe as claimed in claim 1, wherein said piercing means is fitted with a push-rod with four sharp parts.

* * * * *